United States Patent [19]
Baba et al.

[11] Patent Number: 4,930,514
[45] Date of Patent: Jun. 5, 1990

[54] ULTRASONIC IMAGING APPARATUS

[75] Inventors: Tatsuro Baba; Ryoichi Kanda; Yasutsugu Seo, all of Ootawara, Japan

[73] Assignee: Kabushiki Kaisha Toshiba, Kawasaki, Japan

[21] Appl. No.: 228,195

[22] Filed: Aug. 4, 1988

[30] Foreign Application Priority Data

Aug. 12, 1987 [JP] Japan ................. 62-201245

[51] Int. Cl.[5] ............................... A61B 8/06
[52] U.S. Cl. ...................... 128/661.09; 73/861.25
[58] Field of Search ............ 128/661.08–661.10; 73/861.25

[56] References Cited

U.S. PATENT DOCUMENTS

| | | | |
|---|---|---|---|
| 4,607,642 | 8/1986 | Powers | 128/661.09 |
| 4,817,617 | 4/1989 | Taheuchi et al. | 128/661.09 X |
| 4,817,618 | 4/1989 | Des Jardins et al. | 128/661.09 |

FOREIGN PATENT DOCUMENTS

3043047A1 11/1980 Fed. Rep. of Germany.
3637056A1 10/1986 Fed. Rep. of Germany.

OTHER PUBLICATIONS

Lee, MH, et al., "Analysis of a Scan Conversion Algorithm for a Real Time Sector Scanner" IEEE Transactions on Medical Imaging, vol. MI-5, No. 2, Jun. 1986.

Primary Examiner—Francis Jaworski
Attorney, Agent, or Firm—Finnegan, Henderson, Farabow, Garrett and Dunner

[57] ABSTRACT

An ultrasonic imaging apparatus comprises an ultrasonic transducer for emitting ultrasonic pulses at a rate frequency fr and converting an echo wave of the ultrasonic pulses into an echo signal, an orthogonal detector circuit for orthogonally detecting an echo signal provided from the ultrasonic transducer and a calculator circuit for obtaining Doppler data from the orthogonal detection signal and providing color Doppler data. The output of the calculator circuit is coupled to an interpolator circuit. When the interpolator circuit receives color Doppler data at a frequency above $+fr/2$ or $-fr/2$ from the calculator circuit, it interpolates the Doppler data according to a predetermined argorithm for excluding interpolation data corresponding to a zero region between $+fr/2$ and $-fr/2$. The color Doppler data including interpolation data is displayed as color image on the monitor.

16 Claims, 8 Drawing Sheets

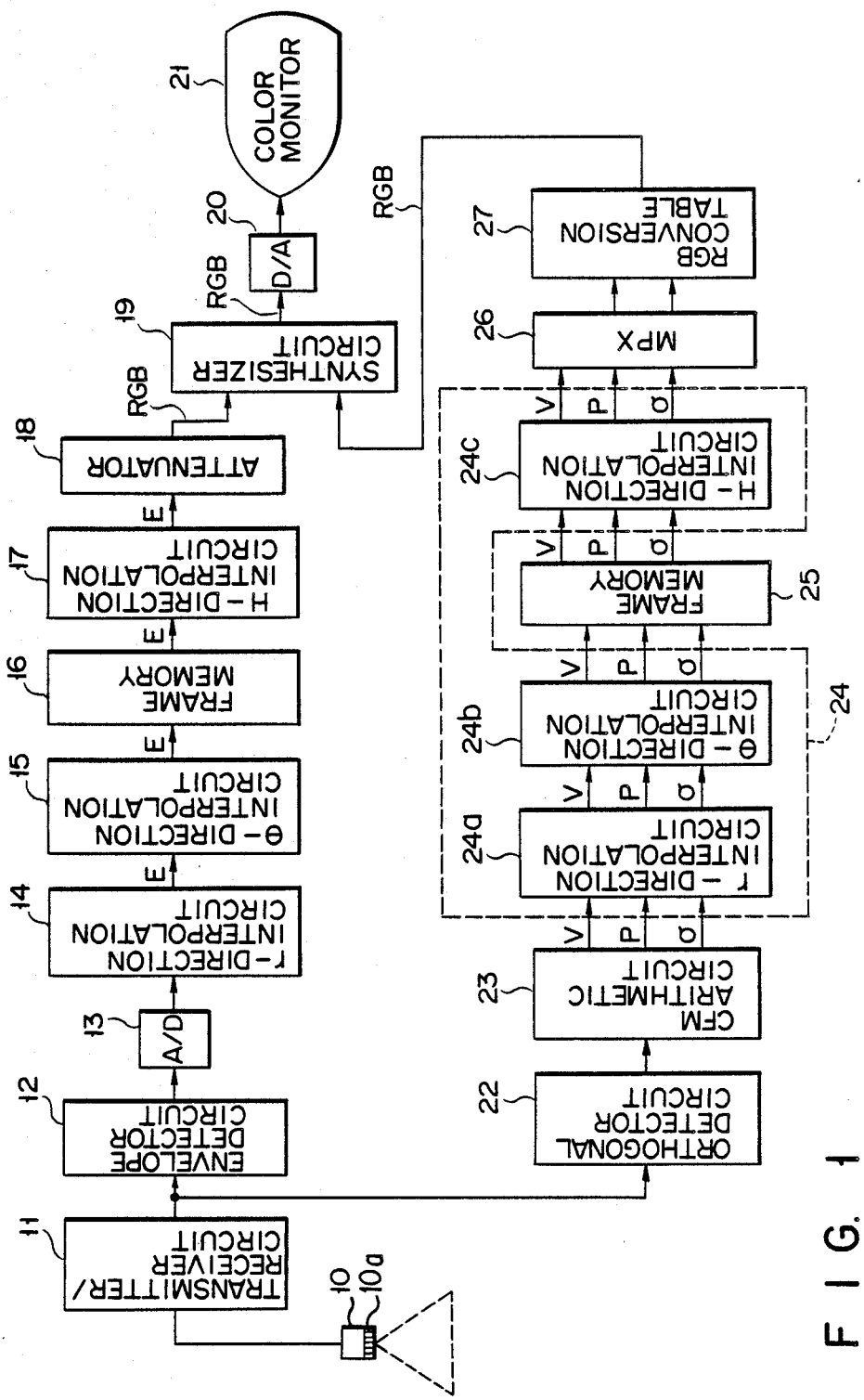
F I G. 1

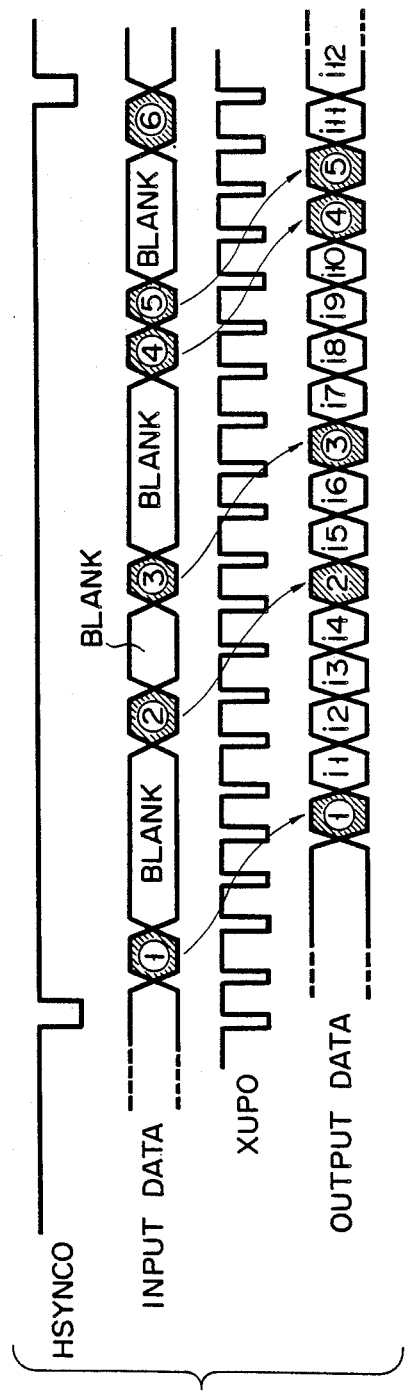
F I G. 12

ULTRASONIC IMAGING APPARATUS

BACKGROUND OF THE INVENTION

1. Field of the Invention

This invention relates to an ultrasonic imaging apparatus for obtaining information of the liquid flow, e.g., blood flow in a living body by utilizing the Doppler effect of ultrasonic waves, and displaying this information as a two-dimensional image.

2. Description of the Related Art

The ultrasonic imaging apparatus uses an ultrasonic Doppler process and a pulse reflection process in combination to generate blood flow data and tomographic image (B mode) data with a single ultrasonic probe and superimpose these data on each other. A superimposed image data is displayed, as a blood flow profile and a tomographic image, on the monitor.

The ultrasonic imaging is based on the following principle.

When a living body, in which blood is flowing, is irradiated with an ultrasonic beam, the center frequency fc thereof is distributed by flowing blood cells and receives a Doppler effect so that it is shifted by fd. That is, the ultrasonic echo resulting after the Doppler effect has a frequency f of f=fc+fd. The frequencies fc and fd are related as $$fd = 2v \cos\theta/c \cdot fc$$

where v is the blood velocity, $\theta$ is the angle between the ultrasonic beam and blood vessel, and c is the velocity of sound.

Thus, the blood velocity v can be obtained by detecting the Doppler shift frequency fd. When measuring the blood flow speed by utilizing the Doppler effect, the living body is irradiated with an ultrasonic pulse directed several times in a predetermined direction from an ultrasonic transducer. The echo pulses of the ultrasonic pulses from the living body, having received the Doppler effect, is received by an ultrasonic transducer to be successively converted to an echo signal. The echo signal is supplied to a phase detector to detect a Doppler shift signal. In this case, a Doppler shift signal is detected with respect to 256 sampling points in a raster direction of the ultrasonic pulses (i.e., depth direction of the living body under examination). The Doppler shift signal that is detected by each sample point is supplied to a frequency analyzer for frequency analysis and then converted by a DSC (digital scan converter) into a scanning signal to be displayed as a two-dimensional blood flow profile image.

When the Doppler shift signal is displayed as a blood flow profile image on the monitor, the mean blood velocity is displayed as an angle ($+\pi$ to $-\pi$) or as a frequency ($+fr/2$ to $-fr/2$). The angle display ($+\pi$ to $-\pi$) or frequency display ($+fr/2$ to $-fr/2$) is in a corresponding color (blue-black-red). fr is the ultrasonic pulse rate frequency.

In the blood flow display by the above color Doppler method, the Doppler shift signal is subjected to a frequency analysis calculation based on the first Fourier transformation (FFT) or color flow mapping (CFM). This calculation is that of the discrete value system referring to the rate frequency. Therefore, when the Doppler signal exceeding $+fr/2$ (or $+\pi$) or $-fr/2$ (or $-\pi$) is supplied to a processor, there occurs an aliasing phenomenon, i.e., a phenomenon, in which the signal of a level exceeding a threshold level of the display is inverted and the excess level portion of the signal is displayed in a color showing a blood flow direction opposite to the normal blood flow direction.

In the color display of the blood flow by the color Doppler method, Doppler image data that is extracted for improving the quality of the color display is interpolated. In the interpolation between two sample data, if interpolation data includes data corresponding to a black level, an image corresponding to an aliasing region is displayed as an image with a black frame. Such an image with a black frame is undesired from the diagnosis standpoint if it is displayed in a blood flow profile image.

SUMMARY OF THE INVENTION

An object of the invention is to provide an ultrasonic imaging apparatus which is free from generation of any frame in the blood flow profile.

According to the invention, there is provided an ultrasonic imaging apparatus, which comprises an ultrasonic transducer for emitting ultrasonic pulses at a rate frequency fr and converting the echo wave of the ultrasonic pulses into an echo signal, a Doppler data output device for receiving the echo signal provided from the ultrasonic transducer, obtaining Doppler data from the echo signal and providing color Doppler data, an interpolating device for receiving color Doppler data from the Doppler data output device when the frequency of the received color Doppler data is above $+fr/2$ or $-fr/2$, the interpolating device interpolates the color Doppler data on the basis of a predetermined argorithm to exclude interpolation data corresponding to a zero region between $+fr/2$ and $-fr/2$. A display is provided for displaying color Doppler data including interpolation data obtained from the interpolating device as a color image.

BRIEF DESCRIPTION OF THE DRAWINGS

FIG. 1 is a block diagram showing an embodiment of the ultrasonic imaging apparatus according to the invention;

FIGS. 10 to 12 are timing charts showing timings of interpolation.

DETAILED DESCRIPTION OF THE PREFERRED EMBODIMENTS

Figure 2:
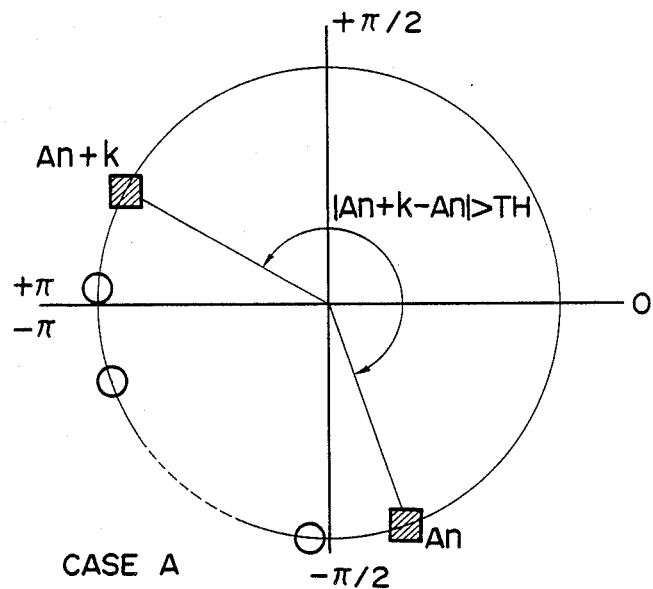
FIGS. 2 to 5 are views for explaining the direction of interpolation.

As shown in FIG. 1, ultrasonic transducer 10 comprises a plurality of ultrasonic transducer elements 10a arranged in an array. Ultrasonic transducer 10 is connected to transmitter/receiver circuit 11, which produces drive pulses for driving ultrasonic transducer 10 and processes an echo signal therefrom. The output terminal of transmitter/receiver circuit 11 is connected to envelope detector circuit 12 and orthogonal detector circuit 22. Envelope detector circuit 12 envelope-detects an echo signal provided from transmitter/- receiver circuit 11, and orthogonal detector circuit 22 effects orthogonal detection of the echo signal.

The output terminal of envelope detector circuit 12 is connected through A/D converter 13 to the input terminal of r-direction interpolation circuit 14. r-direction interpolation circuit 14 interpolates data in an ultrasonic beam raster direction. The output terminal of r-direction interpolation circuit 14 is connected to the input terminal of θ-direction interpolation circuit 15 for interpolating data in an ultrasonic beam scanning direction. The output terminal of θ-direction interpolation circuit 15 is connected to a write terminal of frame memory 16. A read terminal of frame memory 16 is connected to the input terminal of H-direction interpolation circuit 17 for interpolating data in a horizontal scanning direction of a monitor. The output terminal of H-direction interpolation circuit 17 is connected through attenuator 18 to monochrome/color synthesizer circuit 19. Attenuator 18 suitably attenuates the output of the H-direction interpolation circuit and provides the attenuation output to monochrome/color synthesizer circuit 19.

The output terminal of orthogonal detector circuit 22 is connected to the input terminal of CFM calculator circuit 23, which A/D converts the orthogonal detection signal and then frequency-analyzes the resultant digital signal to provide signals representing the mean blood velocity V, total power P and turbulence $\sigma$. The output terminals (V, P and $\sigma$) of CFM calculator circuit 23 are connected to the respective input terminals of r-direction interpolation circuit 24a of data interpolation circuit section 24 for interpolating the output data of CFM calculator circuit 23 in the r-direction. The output terminals (V, P and $\sigma$) of r-direction interpolation interpolator circuit 24a are connected to the respective input terminals of θ-direction interpolation circuit 24b. The output terminals (V, P and $\sigma$) of θ-direction interpolation circuit 24a are connected to the respective input terminals of θ-direction interpolation circuit 24b. The output terminals (V, P and $\sigma$) of θ-direction interpolation circuit 24b are connected to the response write terminals of color frame memory 25. The read terminals (V, P, $\sigma$ and $\alpha$) of color frame memory 25 are connected to H-direction interpolation circuit 24c for interpolating data in the horizontal scanning direction of the monitor according to data frame memory 25.

r-, θ- and H-direction interpolation circuits 24a, 24b and 24c each perform an interpolation calculation at a signal level, at which the aliasing phenomenon occurs, after rules to be described later.

The output terminal of H-direction interpolation circuit 24c is connected through multiplexer 26 to RGB conversion table 27. RGB conversion table 27 converts a Doppler image signal obtained through multiplexer 26 into a RGB video signal which is supplied to monochrome/color synthesizer circuit 19. Monochrome/color synthesizer circuit 19 synthesizes the B mode signal obtained through attenuator 17 and color Doppler signal obtained through RGB conversion table 27 and provides the result signal through D/A converter 20 to monitor 21.

Data interpolation circuit section 24 will now be further described.

Data interpolation circuit section 24 performs data interpolation using interpolation algorithms as shown in the Table below.

| Condition 1 | Condition 2 | Condition 3 | Intermediate Interpolation Output | Case |
|---|---|---|---|---|
| $\|Am - An\| > TH$ | Am and An are of opposite signs | $An + Am \geq 0$ | $\dfrac{-fr}{2} + \dfrac{An + Am}{2}$ | A |
| | | $An + Am < 0$ | $\dfrac{fr}{2} + \dfrac{Am + An}{2}$ | B |
| | Am and An are of the same sign | Unnecessary because of use in the condition $TH > fr/2$ | | |
| $\|Am - An\| \leq TH$ | | | $\dfrac{Am + An}{2}$ | C |

Referring to the Table above, the calculation is performed with respect to a mid point between two points (An and Am) or a point near the mid point. Where there are a large number of interpolation points, the calculation is repeatedly performed between point An and mid point and between mid point and point Am.

Condition 1 is a check concerning the magnitude relationship between the threshold level TH that can be varied by the user and the absolute value of the difference between Am and An. Condition 2 is a check as to whether Am and An are of the same sign. Condition 3 is a check of the sign of the sum of Am and An.

Figure 3:
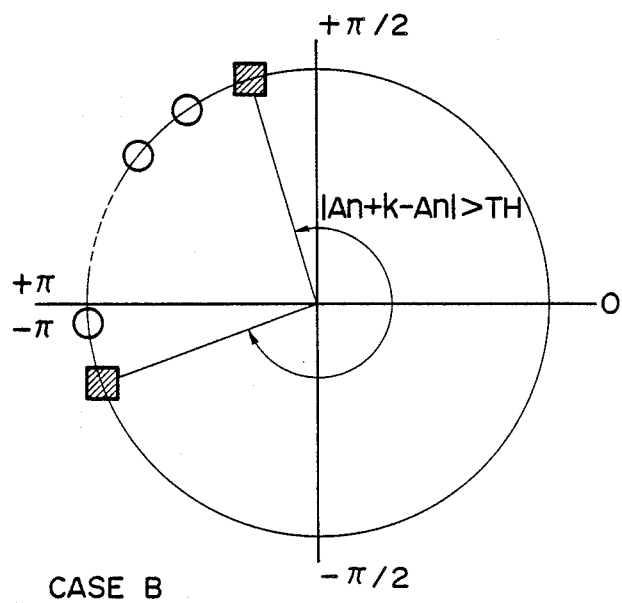
Figure 4:
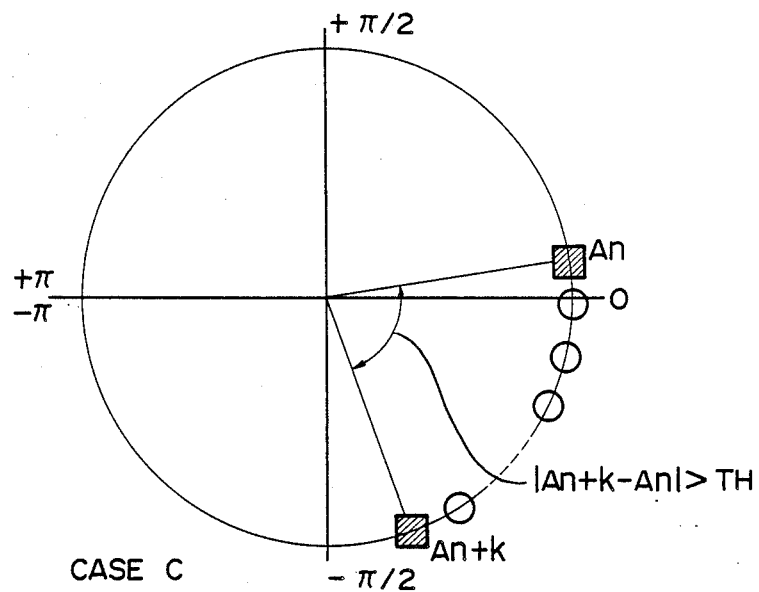
Figure 5:
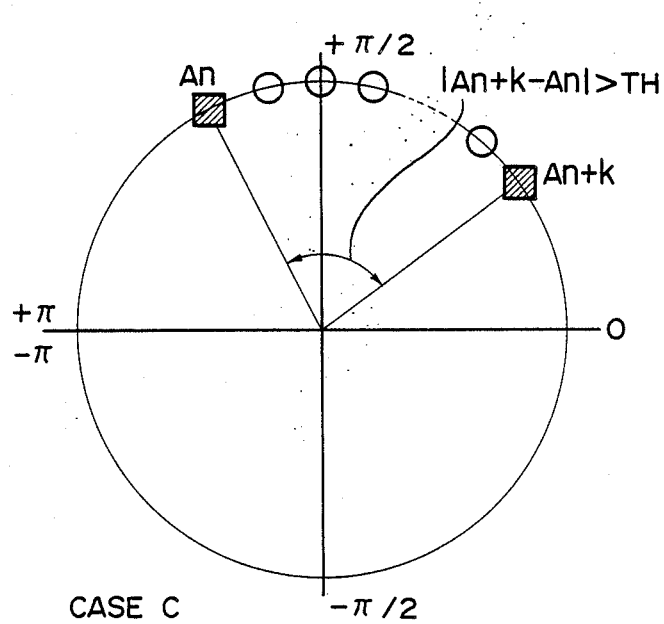

FIGS. 2 and 3 show the directions of interpolation in cases A and B in the Table, and FIGS. 4 and 5 show the direction of interpolation in case C.

Figure 6:
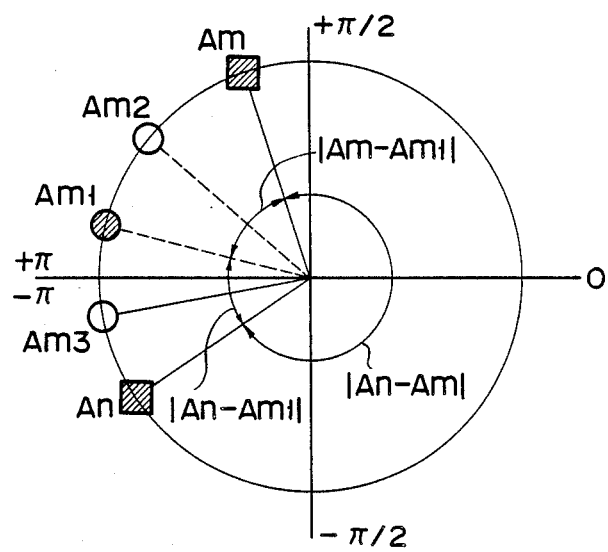
FIG. 6 is a view for explaining the logic of interpolation.

The interpolation logic will now be described in detail with reference to FIG. 6.

In condition 1, the relationship between An and Am is $|Am - An| = TH$ (where $TH \geq fr/2$)

Likewise, in condition 2 Am and An are of different signs, and in condition 3 they are related as $Am + An < 0$ Thus, the mid point Am1 is $Am1 = fr/2 + (Am + An)/2$ Now, the mid point Am3 between points Am1 and An obtained in the same way as above is obtained as follows.

In condition 1, the following relationship exists $|Am1 - An| > TH$

In condition 2, Am1 and An have different signs.

In condition 3, the following relationship exists $$An + Am1 < 0$$

Thus, the mid point Am3 between points An and Am1 is expressed as $$Am3 = -fr/2 + (An + Am1)/2$$

The mid point Am2 between points Am1 and Am is obtained as follows.
In condition 1, the following relationship exists $$|Am1 - An| > TH$$

Thus, Am2 is expressed as $$Am2 = (An + Am1)/2$$

Now, the operation of the embodiment shown in FIG. 1 will be described.

Ultrasonic transducer 10 receives drive pulses transmitter/receiver circuit 11 and scans the living body under examination with an ultrasonic beam. The echo wave of the ultrasonic wave beam from the living body is converted into the echo signal by ultrasonic transducer 10. The echo signal is supplied to envelope detector circuit 12 for envelope-detection. A/D converter 13 samples the detection signal and converts it into a corresponding digital signal which is supplied to r-direction interpolation circuit 14.

r-direction interpolation circuit 14 interpolates the digital image data from A/D converter 13 in the r-direction, i.e., beam raster direction. More particularly, the gap between adjacent sampled data is interpolated with interpolation data. The output data of r-direction interpolation circuit 14 is supplied to θ-direction interpolation circuit 15. θ-direction interpolation circuit 15 interpolates data in the scanning direction. That is, the interval between adjacent ultrasonic beams is interpolated with interpolation data. The digital image data, i.e., B mode image data, from θ-direction interpolation circuit 15, is stored in frame memory 16. When the image data read out from frame memory 16 is supplied to H-direction interpolation circuit 17, interpolation is performed in the horizontal scanning direction of the monitor, which has not been interpolated in the θ-direction. The output image data from H-direction interpolation circuit 17 is connected to attenuator 18 and then supplied through synthesizer circuit 19 and D/A converter 20 to monitor 21, whereby a B mode image is displayed on monitor 21.

When obtaining the Doppler signal, transmitter/receiver circuit 22 provides eight drive pulses to ultrasonic transducer 10, and ultrasonic transducer 10 provides eight ultrasonic pulses. The echo wave of the ultrasonic pulses is converted by ultrasonic transducer 10 into an echo signal to be supplied to orthogonal detector circuit 22. Orthogonal detector circuit 22 effects orthogonal detection of the echo signal to produce a Doppler shift frequency signal. This Doppler shift frequency signal is supplied to the CFM calculator circuit 23 for frequency analysis. CFM calculator circuit 23 frequency-analyzes the Doppler shift frequency signal to obtain the mean flow velocity V, total power P and turbulence σ. These data V, P and σ are interpolated in the r-direction by r-direction interpolation circuit 24a and also interpolated in the θ-direction by θ-direction interpolation circuit 24b.

The data V, P and σ provided from θ-direction interpolation circuit 24b are stored in frame memory 25. The data V, P, σ and α read out from frame memory 25 are supplied through multiplexer 26 to RGB conversion table 27. The data P, π and α, i.e., Doppler data, are converted by the RGB conversion table into a RGB signal supplied to monochrome/color synthesizer circuit 19. Synthesizer circuit 19 synthesizes the B mode data and Doppler data and supplies the resultant data through D/A converter 20 to color monitor 21. Thus, the B mode data and the color image showing the blood flow are superimposed for on each other for displayed on color monitor 21.

Figure 8:
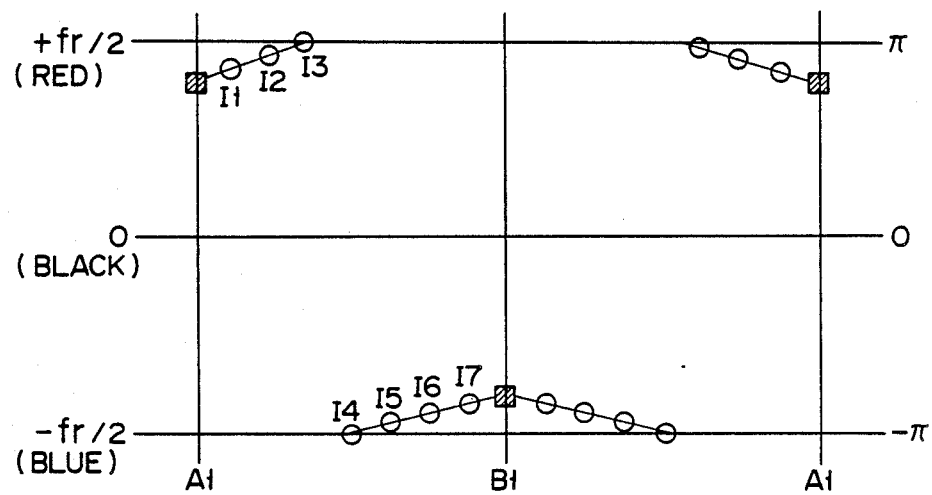
FIG. 8 is a view for explaining an interpolation argorithm.
Figure 7:
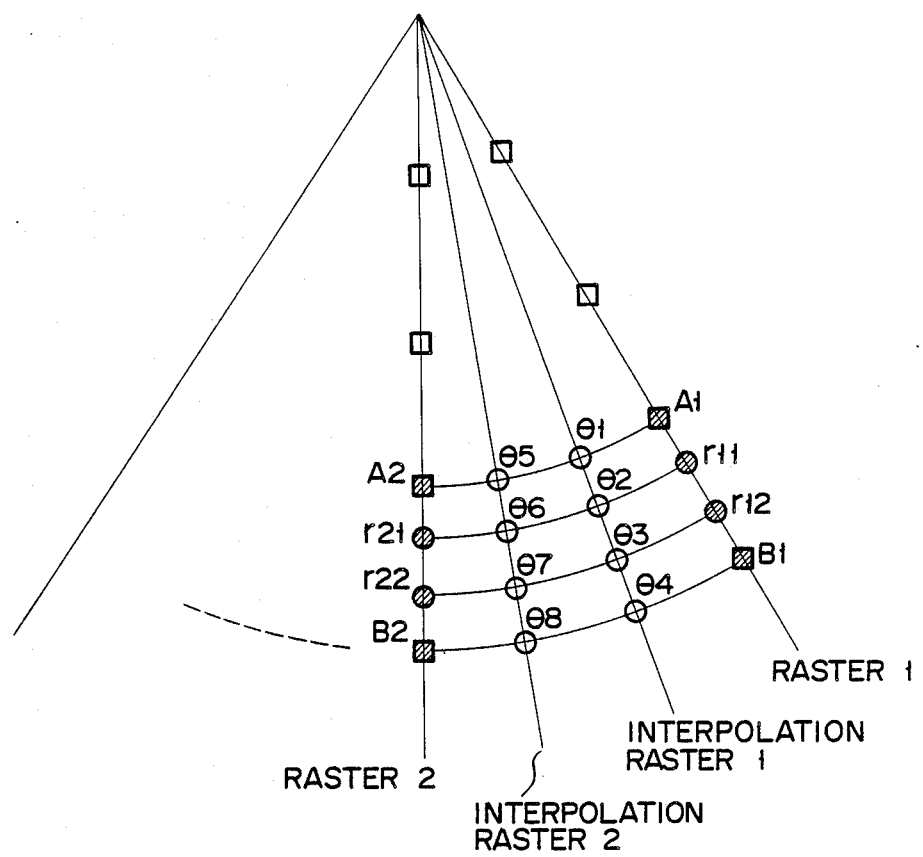
FIG. 7 is a view for explaining interpolation in sector scanning.

Now, the interpolation in the r-, θ- and H-directions will be described with reference to FIGS. 7 and 8. Referring to FIG. 7, when raster 1 is obtained from sample data A1 and B1, interpolation data of r11 and r12 are obtained through interpolation in the r-direction. When data A2 and B2 on raster 2 are sampled, interpolation data r21 and r22 are obtained through interpolation in the r-direction. With sampled data A1, A2, B1 and B2 and interpolation data r11, r12, r21 and r22 interpolation is done in the θ-direction along concentric circles in the sector scan. Thus, interpolation data θ1 to θ4 and θ5 to θ8.

In the above interpolation, it is assumed that interpolation data is obtained ordinarily from sampled data A1 and B1 when the data A1 and B1 respectively represent red color (+) and blue color (−), for instance. In this case, if A1 = B1, the interpolation data is zero since B1 is −A1. Accordingly, the interpolation data is expressed as a black frame. In this embodiment, however, the interpolation is carried out on the basis of case A shown in the above Table. That is, the interpolation data is obtained as −fr/2 = (A1 + B1)/2. Thus, if A1 = B1, the interpolation data is −fr/2 so that it is displayed as blue color. Where the sample data A1 and B1 respectively represent blue color (−) and red color (+), A1 = B1, the interpolation data is not zero, so that no black frame is provided. FIG. 8 shows this case. It will be seen that the interpolation data never becomes zero.

Figure 9:
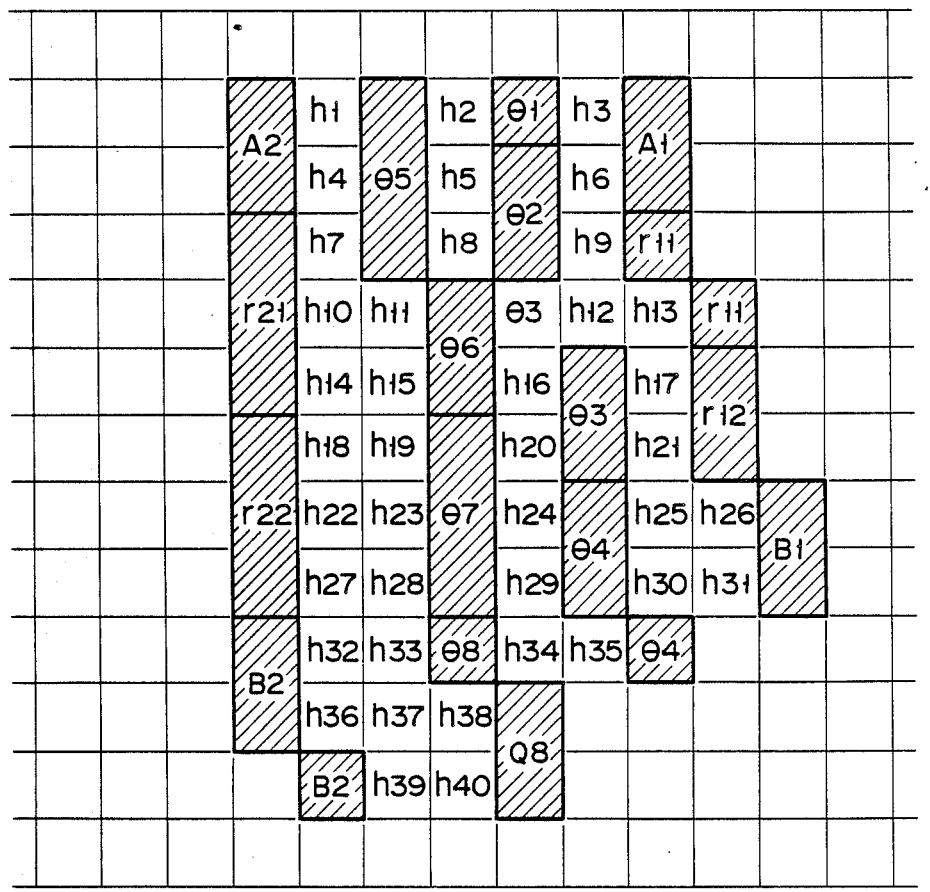
FIG. 9 is a view showing a frame memory, in which sample data and interpolation data are stored.

When the r- and θ-direction interpolation data obtained in the above way are stored together with the sampled data in the frame memory, they are stored in corresponding memory elements as shown shaded in FIG. 9. In this case, no data is present memory elements other than those, in which the sampled data and r- and θ-direction interpolation data are stored. Thus, when image data is read out from the frame memory, interpolation (i.e., H-direction interpolation) is performed in the horizontal scanning direction of the monitor, and interpolation data h1 to h40 are stored in vacant memory elements.

If the data for interpolation are B mode image data and data representing the variance value σ, these data have no signs, so that the interpolation is performed on the basis of case D.

Now, the timing of interpolation will be described with reference to FIGS. 10 to 12.

Figure 10:
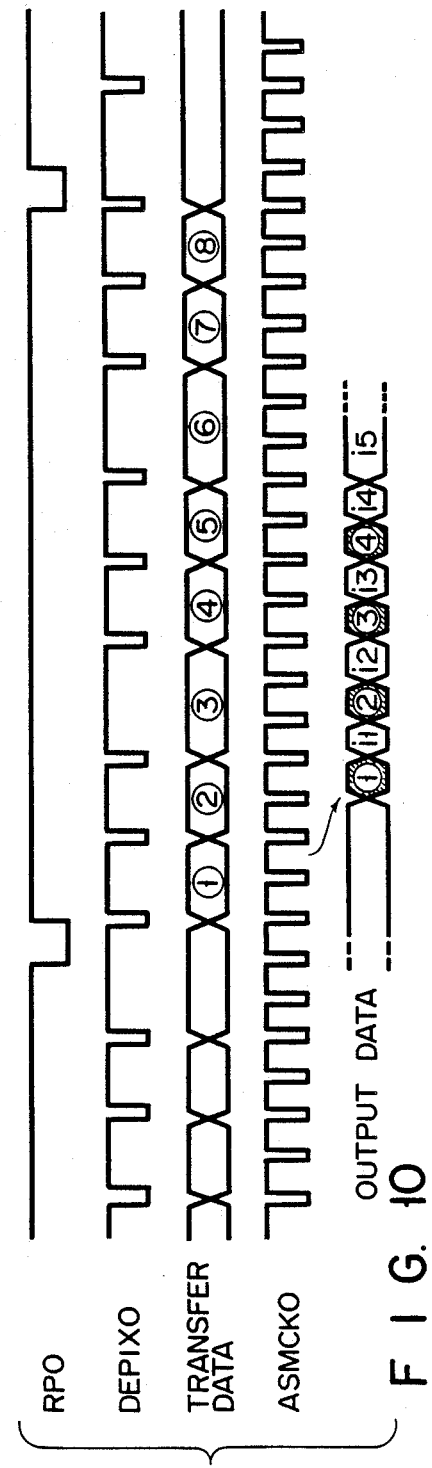

FIG. 10 shows the timing of interpolation in the r-direction. In the period (pulse period) of a start timing clock (rate) of first raster 1, transfer data ① to ⑧ are transferred from CFM calculator circuit 23 to interpolator circuit 24 in response to transfer clock DFPIXO. At this time, the transfer data ① to ⑧ are sampled in response to the sampling clock, and sample data are used for interpolation in the r-direction. In this interpolation, interpolation data i1 to i4 are produced in an interpolation relationship to sampled data ①  to ④.

Figure 11:
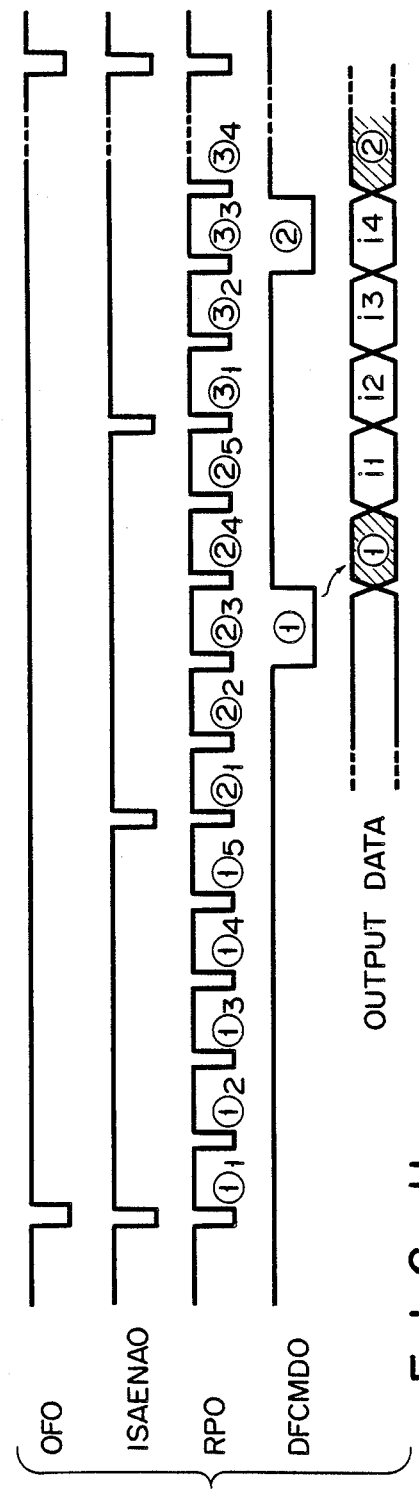

FIG. 11 shows the timing of interpolation in the θ-direction. Labeled OFO is one scan signal due to ultrasonic beam scanning. Five rate pulses RPO are produced in each pulse interval of timing pulse signal ISENAO. With this timing signal the same raster is scanned five times in the θ-direction scanning before the scanning of the next raster. Thus, raster image signals ①1 to ①5 are generated for each pulse of signal ISAENAO. In this scanning, CFM calculator circuit 23 produces raster data ①, ② each for every five pulses of signal RPO under control of timing signal DFCMDO. The image of the raster data is the same as output data for one line shown in FIG. 10, and interpolation data i1 to i4 are formed for the corresponding pixels.

FIG. 12 shows the timing of interpolation in the H-direction. Labeled HSYNCO is a signal for reading out data in the horizontal direction of the frame memory. When data read out from the frame memory during the pulse period of signal HSYNCO is transferred to multiplexer 26, H-direction interpolation circuit 24c effects an interpolation calculation, whereby interpolation data i1 to i12 to be inserted in vacant pixels among read-out data ①, ②, ... are generated in synchronism to read-out transfer clock XUPO.

As has been shown in the foregoing, according to the invention interpolation data is generated in accordance with a predetermined interpolation argorithm, so that no black level data is contained in the interpolation data even is a signal at a level, at which the aliasing phenomenon occurs, is input. Hence, there is no possibility of formation of a black frame in a blood flow profile displayed on the monitor.

In the above embodiment, the interpolation circuit calculates the interpolation data according to an argorithm shown in the table. However, the interpolation circuit may be comprised as follows. That is, the interpolation data are pre-calculated according to the argorithm, and the interpolation data obtained by the calculation are stored in a ROM. When the sampled data is input to the interpolation circuit, the interpolation data is read out from the ROM according to the sampled data. In this case, the sampled data and the data corresponding to to-be-interpolated points between the sampling data are used as address data. The interpolation data is read out from ROM by the address data.

What is claimed is:

1. An ultrasonic imaging apparatus comprising:
    ultrasonic transducer means for emitting ultrasonic pulses at a rate frequency fr and converting echo waves of said ultrasonic pulses into echo signals;
    Doppler data output means for receiving the echo signals from said ultrasonic transducer means, for obtaining Doppler data from said echo signals and providing color Doppler data;
    interpolating means for receiving said color Doppler data from said Doppler data output means and interpolating said color Doppler data according to a predetermined algorithm to provide interpolation data, and to exclude interpolation data corresponding to a zero region between $+fr/2$ and $-fr/2$ when the frequency of the received color Doppler data is above $+fr/2$ or $-fr/2$; and
    means for displaying said color Doppler data and said interpolation data obtained from said interpolating means as a color image.

2. An ultrasonic imaging apparatus according to claim 1, further comprising frame memory means for storing said Doppler data, and wherein said interpolating means includes means for interpolating data in a direction corresponding to a horizontal readout direction from said frame memory means.

3. An ultrasonic imaging apparatus according to claim 1, wherein said Doppler data output means includes orthogonal detection means for orthogonally detecting an echo signal from said ultrasonic transducer means and means for frequency-analyzing a Doppler shift frequency signal obtained from said orthogonal detection means to provide said Doppler data.

4. An ultrasonic imaging apparatus according to claim 1, wherein said Doppler data output means provides Doppler data including Doppler data components corresponding to sampled data in a predetermined direction, and wherein
    (a) said interpolating means provides interpolation data in accordance with the algorithm:

$$\frac{-fr}{2} + \frac{An + Am}{2}$$

when $|Am-An|>TH$, Am and An have opposite signs and $An+Am \geq 0$;
    (b) said interpolating means provides interpolation data in accordance with the algorithm:

$$\frac{fr}{2} + \frac{Am + An}{2}$$

when $|Am-An|>Th$, Am and An have opposite signs, and $An+Am<0$; and
    (c) said interpolating means provides interpolation data in accordance with the algorithm;

$$\frac{Am + An}{2}$$

when $|Am-An| \leq TH$;
    where Am and An are two adjacent Doppler data components and TH is a threshold level of display.

5. An ultrasonic imaging apparatus according to claim 4, wherein said interpolating means includes means for interpolating data in a direction (r) of emission of ultrasonic pulses and means for interpolating data in a scanning direction (θ) of ultrasonic pulses.

6. An ultrasonic imaging apparatus according to claim 4, wherein $TH \geq fr/2$.

7. An ultrasonic imaging apparatus comprising:
    ultrasonic transducer means for emitting ultrasonic pulses at a rate frequency fr and converting echo waves of said ultrasonic pulses into echo signals;
    Doppler data output means for receiving the echo signals from said ultrasonic transducer means, for obtaining Doppler data from said echo signals and provided color Doppler data;
    interpolating means for receiving said color Doppler data from said Doppler data output means and interpolating said color Doppler data on the basis of a predetermined algorithm to provide interpolation data, and to exclude interpolation data corresponding to a zero region between $+fr/2$ and −fr/2 when the frequency of the received color Doppler data is above +fr/2 or −fr/2;

B mode signal output means for converting the echo signal provided from said ultrasonic transducer means into a B mode image signal;

signal processing means for processing the B mode image signal provided from said B mode signal output means to provide a B mode video signal;

synthesizing means for synthesizing the B mode video signal provided from said signal processing means and said color Doppler data obtained from said interpolating means to provide a resultant signal; and means for displaying the resultant signal obtained from said synthesizing means as a composite image consisting of a B mode image and said color Doppler data.

8. An ultrasonic imaging apparatus according to claim 7, further comprising frame memory means for storing said Doppler data, and wherein said interpolating means includes means for interpolating data in a direction corresponding to a horizontal readout direction from said frame memory means.

9. An ultrasonic imaging apparatus according to claim 7, wherein said Doppler data output means includes orthogonal detection means for orthogonally detecting an echo signal from said ultrasonic transducer means and means for frequency-analyzing a Doppler shift frequency signal obtained from said orthogonal detection means to provide said Doppler data.

10. An ultrasonic imaging apparatus according to claim 7, wherein said signal processing means includes B mode signal interpolating means for interpolating said B mode image signal provided from said B mode signal output means.

11. An ultrasonic imaging apparatus according to claim 10, wherein said B mode signal interpolating means includes means for interpolating the B mode image signal in a direction (r) of emission of ultrasonic pulses and means for interpolating the B mode image signal in a scanning direction (θ) of ultrasonic pulses.

12. An ultrasonic imaging apparatus according to claim 10, wherein said signal processing means further includes frame memory means for storing said B mode image signal, and said B mode signal interpolating means includes means for interpolating data in a direction corresponding to the horizontal read-out direction from said frame memory.

13. An ultrasonic imaging apparatus according to claim 7, wherein said Doppler data output means provides Doppler data including Doppler data components corresponding to sampled data in a predetermined direction, and wherein (a) said interpolating means provides interpolation data in accordance with the algorithm:

$$\frac{-fr}{2} + \frac{An + Am}{2}$$

when $|Am-An|>TH$, Am and An have opposite signs and $An+Am \geq 0$;

(b) said interpolating means provides interpolation data in accordance with the algorithm:

$$\frac{fr}{2} + \frac{Am + An}{2}$$

when $|Am-An|>Th$, Am and An have opposite signs, and $An+Am<0$; and (c) said interpolating means provides interpolation data in accordance with the algorithm:

$$\frac{Am + An}{2}$$

when $|Am-An| \leq TH$ where Am and An are two adjacent Doppler data components and TH is a threshold level of display.

14. An ultrasonic imaging apparatus according to claim 13, wherein said interpolating means includes means for interpolating data in a direction (r) of emission of ultrasonic pulses and means for interpolating data in a scanning direction (θ) of ultrasonic pulses.

15. An ultrasonic imaging apparatus according to claim 13, wherein $TH \geq fr/2$.

16. An ultrasonic imaging apparatus according to claim 7, wherein said B mode signal output means includes means for envelope-detecting the echo signal from said ultrasonic transducer means.

* * * * *